US010342623B2

(12) United States Patent
Huelman et al.

(10) Patent No.: US 10,342,623 B2
(45) Date of Patent: Jul. 9, 2019

(54) SURGICAL GUIDANCE SYSTEMS, DEVICES, AND METHODS

(71) Applicants: Justin Huelman, Lino Lakes, MN (US); Andrew Wu, Taipei (TW); Michael Jung, Chicago, IL (US); Marc Child, San Francisco, CA (US); Vidit Sharma, Rochester, MN (US); Addason Mccaslin, Chicago, IL (US); PROXIMED, LLC, Chicago, IL (US)

(72) Inventors: Justin Huelman, Lino Lakes, MN (US); Andrew Wu, Taipei (TW); Michael Jung, Chicago, IL (US); Marc Child, San Francisco, CA (US); Vidit Sharma, Rochester, MN (US); Addason Mccaslin, Chicago, IL (US)

(73) Assignee: PROXIMED, LLC, Chicago, IL (US)

( * ) Notice: Subject to any disclaimer, the term of this patent is extended or adjusted under 35 U.S.C. 154(b) by 253 days.

(21) Appl. No.: 14/917,896

(22) PCT Filed: Mar. 12, 2015

(86) PCT No.: PCT/US2015/020152
§ 371 (c)(1),
(2) Date: Mar. 9, 2016

(87) PCT Pub. No.: WO2015/138708
PCT Pub. Date: Sep. 17, 2015

(65) Prior Publication Data
US 2016/0220314 A1    Aug. 4, 2016

Related U.S. Application Data

(60) Provisional application No. 61/951,543, filed on Mar. 12, 2014.

(51) Int. Cl.
*A61B 34/20* (2016.01)
*A61B 17/00* (2006.01)
(Continued)

(52) U.S. Cl.
CPC .... *A61B 34/20* (2016.02); *A61B 2017/00022* (2013.01); *A61B 2017/00119* (2013.01);
(Continued)

(58) Field of Classification Search
CPC ............ A61B 34/20; A61B 2562/0223; A61B 2034/2051; A61B 3/20; A61B 90/37
(Continued)

(56) References Cited

U.S. PATENT DOCUMENTS 4,790,809 A   12/1988 Kuntz
5,080,104 A   1/1992 Marks et al.
(Continued)

FOREIGN PATENT DOCUMENTS

EP   1181895 A2   2/2002
EP   1264404 B1   8/2003
JP   4564840 B2   10/2010

OTHER PUBLICATIONS

International Search Report and Written Opinion, corresponding International Application No. PCT/US2015/020152, dated Jun. 4, 2015.

*Primary Examiner* — Suzette J Gherbi
(74) *Attorney, Agent, or Firm* — Marshall, Gerstein & Borun LLP

(57) ABSTRACT

Surgical systems and methods for avoiding injury to an anatomical structure are disclosed. According to some aspects, an implantable device configured to emit a detectable field may be attached to the anatomical structure. A proximity sensor may be attached to a distal end of a surgical instrument and may be configured to detect the detectable (Continued)

field. A control unit in communication with the proximity sensor may be configured to use the proximity sensor to determine if the distal end of the surgical instrument is within a predetermined distance of the implantable device. If so, a notification such as a vibration or alarm may be provided to a user of the surgical instrument so that the user can maneuver the surgical instrument to limit or prevent contact with the anatomical structure.

22 Claims, 7 Drawing Sheets

(51) Int. Cl.
*A61B 17/42* (2006.01)
*A61B 90/00* (2016.01)

(52) U.S. Cl.
CPC .......... *A61B 2017/00876* (2013.01); *A61B 2017/4216* (2013.01); *A61B 2034/2051* (2016.02); *A61B 2034/2072* (2016.02); *A61B 2090/3954* (2016.02); *A61B 2562/0223* (2013.01); *A61B 2562/0257* (2013.01)

(58) Field of Classification Search
USPC .......................................... 600/191
See application file for complete search history.

(56) References Cited

U.S. PATENT DOCUMENTS

| | | |
|---|---|---|
| 5,282,784 A | 2/1994 | Willard |
| 5,423,321 A | 6/1995 | Fontenot |
| 5,503,320 A | 4/1996 | Webster et al. |
| 5,519,317 A | 5/1996 | Guichard et al. |
| 6,216,028 B1* | 4/2001 | Haynor .................... A61B 5/06 128/899 |
| 7,099,712 B2 | 8/2006 | Fuimaono et al. |
| 8,060,214 B2 | 11/2011 | Larson et al. |
| 8,295,912 B2* | 10/2012 | Gertner .................... A61B 8/06 600/424 |
| 8,374,673 B2* | 2/2013 | Adcox .................... A61B 34/20 600/410 |
| 8,617,155 B2 | 12/2013 | Johnson et al. |
| 8,623,004 B2 | 1/2014 | Johnson et al. |
| 2005/0027199 A1 | 2/2005 | Clarke |
| 2006/0124140 A1* | 6/2006 | Forsell .................... A61B 5/06 128/899 |
| 2013/0131500 A1 | 5/2013 | Sharonov |
| 2013/0190598 A1 | 7/2013 | Sharonov et al. |
| 2015/0238685 A1* | 8/2015 | Elias .................... A61M 25/007 600/420 |
| 2016/0015469 A1* | 1/2016 | Goshayesh ............... G06T 7/11 600/424 |

* cited by examiner

SURGICAL GUIDANCE SYSTEMS, DEVICES, AND METHODS

CROSS-REFERENCE TO RELATED APPLICATIONS

The present application is a U.S. national stage application of International Patent Application No. PCT/US2015/020152, filed Mar. 12, 2015, which application claims priority to U.S. Provisional Patent Application No. 61/951,543, filed Mar. 12, 2014. The contents of each of these applications are herein incorporated by reference in their entirety.

FIELD OF DISCLOSURE

The present disclosure generally relates to devices, methods, and systems for guiding a surgical instrument during a surgical procedure, and more particularly, notifying or alerting a surgeon of the proximity of a surgical instrument to an anatomical structure so that the surgeon can more precisely guide interaction with and/or avoid unintentional injury to the anatomical structure.

BACKGROUND

A common surgical objective is to avoid unintentional injury to the patient. Oftentimes the anatomical structures (e.g., tissues, organs, vessels, etc.) of interest are surrounded by fatty tissue and other non-target anatomical structures. These objects can obscure the field of view of the surgeon and thus increase the difficulty of identifying the anatomical structures of interest.

Other factors may further complicate this task. In laparoscopic procedures, for example, a three-dimensional space is shown to the surgeon on a two-dimensional display, thereby distorting depth perception and location measurements. Furthermore, even in successful surgical procedures, the surgical site is oftentimes submerged in blood, making it difficult to distinguish between different anatomical structures. In surgical procedures having an obstructed field of view, a surgeon must rely on his or her anatomical knowledge and/or trial-and-error to locate the anatomical structures of interest.

Once the target anatomical structure(s) are identified, it may still be necessary to avoid contact with non-target anatomical structures to prevent unintended injury to the patient. Avoiding contact with non-target anatomical structures can be difficult for reasons similar to those discussed above. Accordingly, identifying anatomical structures of interest and avoiding contact with non-target anatomical structures is oftentimes very difficult and may depend largely on the skill and experience of the surgeon.

Unintentional injury to non-target anatomical structures can result in serious complications during the surgical procedure, increasing both morbidity and mortality rates. Thus, a need exists for the ability to spatially locate surgical instruments and other medical devices relative to anatomical structures and/or other medical devices.

One common unintentional injury associated with open and/or laparoscopic surgeries is injury to the ureter. Ureteral injuries often occur during abdominal surgical procedures such as obstetrics/gynecology (OB/GYN) procedures, colorectal procedures, and urology procedures. Recent studies have found that ureteral injury occurs in up to 2.0% of hysterectomies. Since up to 700,000 hysterectomies are performed in the United States on an annual basis, the number of unintentional ureteral injuries is significant.

To avoid unintentional injury to a non-target anatomical structure, it is helpful to know the location of the non-target anatomical structure. The ureter is surrounded by peritoneal tissue and other vessels that run roughly parallel to the ureter. As a result, the ureter is sometimes mistaken for other vasculature in its vicinity. In complicated cases, there may be scar tissue, tumoral masses, and/or other obstructions that increase the difficulty of identifying the ureter. Successful patient outcomes are therefore largely dependent on the surgeon's knowledge, skill, and familiarity with the surgical procedure. Ureteral injuries, if not detected during surgery, may result in serious complications including formation of ureterovaginal fistulas and potential loss of kidney function.

In some cases, a surgeon may employ one or more medical devices to help identify the location of the ureter. For instance, as preliminary step, a surgeon may insert a simple stent into the ureter. Subsequently, the rigidity of the stent allows the surgeon to feel for the ureter by hand. However, this method is only useful in open surgeries, where the surgeon can freely feel around the surgical area.

Some known ureteral stents integrate a lighting system that extends down the body of the stent and which can shine light through tissue for marking the location of the ureter. However, the light may be difficult to see in certain patients and generally is visible only through a limited layer of obstruction. Furthermore, the increased width and rigidity of lighted ureteral stents makes their insertion difficult and can deform the natural orientation of the ureter. This may render the ureter more prone to injury. Lighted ureteral stents are also significantly more expensive than unlighted ureteral stents.

Other visualization systems, such as infrared mapping systems or biochemically engineered dyes, may be used to locate the ureter. However, these systems typically require expensive equipment, as well as extra training, preparation, and maintenance.

To summarize, unintentional contact and injury to non-target anatomical structures occur in a wide variety of surgeries. Accordingly, a need exists for improved devices, methods, and systems for determining the location of surgical instruments and other medical devices relative to target and non-target anatomical structures.

SUMMARY

One aspect of the present disclosure provides a surgical guidance system including an implantable device, a surgical instrument, a proximity sensor, and a control unit. The implantable device may be configured for attachment to an anatomical structure and to emit a detectable field. The surgical instrument may include a proximal end and a distal end, and may be movable relative to the implantable device. The proximity sensor may be attached to the distal end of the surgical instrument and may be configured to detect the detectable field. The control unit may be in communication with the proximity sensor and may be configured to use the proximity sensor to determine if the distal end of the surgical instrument is within a predetermined distance of the implantable device.

Another aspect of the present disclosure provides an implantable device for marking a location of an anatomical structure. The implantable device includes a body configured for attachment to the anatomical structure. The implantable device also includes a beacon configured to emit a detectable field having an intensity that varies with distance.

Yet another aspect of the present disclosure provides a surgical method of: (i) introducing an implantable device into a patient and attaching the implantable device to an anatomical structure, the implantable device being configured to emit a detectable field having an intensity that varies with distance; (ii) introducing a distal end of a surgical instrument into the patient and advancing the distal end of the surgical instrument toward the implantable device; (iii) detecting, with a proximity sensor attached to the distal end of the surgical device, the intensity of the detectable field as the distal end of the surgical instrument is advanced toward the implantable device; (iv) determining, with a control unit in communication with the proximity sensor, if the distal end of the surgical instrument is within a predetermined distance of the implantable device based on the intensity of the detectable field; and (v) receiving a notification that the distal end of the surgical instrument is within a predetermined distance of the implantable device.

Another aspect of the present disclosure provides a surgical device including a proximal end configured to be positioned exterior to a patient during a surgical procedure, and a distal end configured to be introduced inside the patient during the surgical procedure. The surgical device may include a proximity sensor attached to the distal end of the surgical device and configured to detect a detectable field emitted by a beacon implanted inside the patient. The surgical device may also include a notification unit attached to the proximal end of the surgical instrument and configured to notify a user of the surgical device that the distal end of the surgical instrument is within a predetermined distance of the beacon.

DETAILED DESCRIPTION

Although the following text sets forth a detailed description of numerous different embodiments, the claims set forth at the end of this application are not limited to the disclosed embodiments. The detailed description is to be construed as exemplary only and does not describe every possible embodiment of the invention since describing every possible embodiment is impractical. Numerous alternative embodiments can be implemented, using either current technology or technology developed after the filing date of this application, which would still fall within the scope of the claims.

Figure 1:
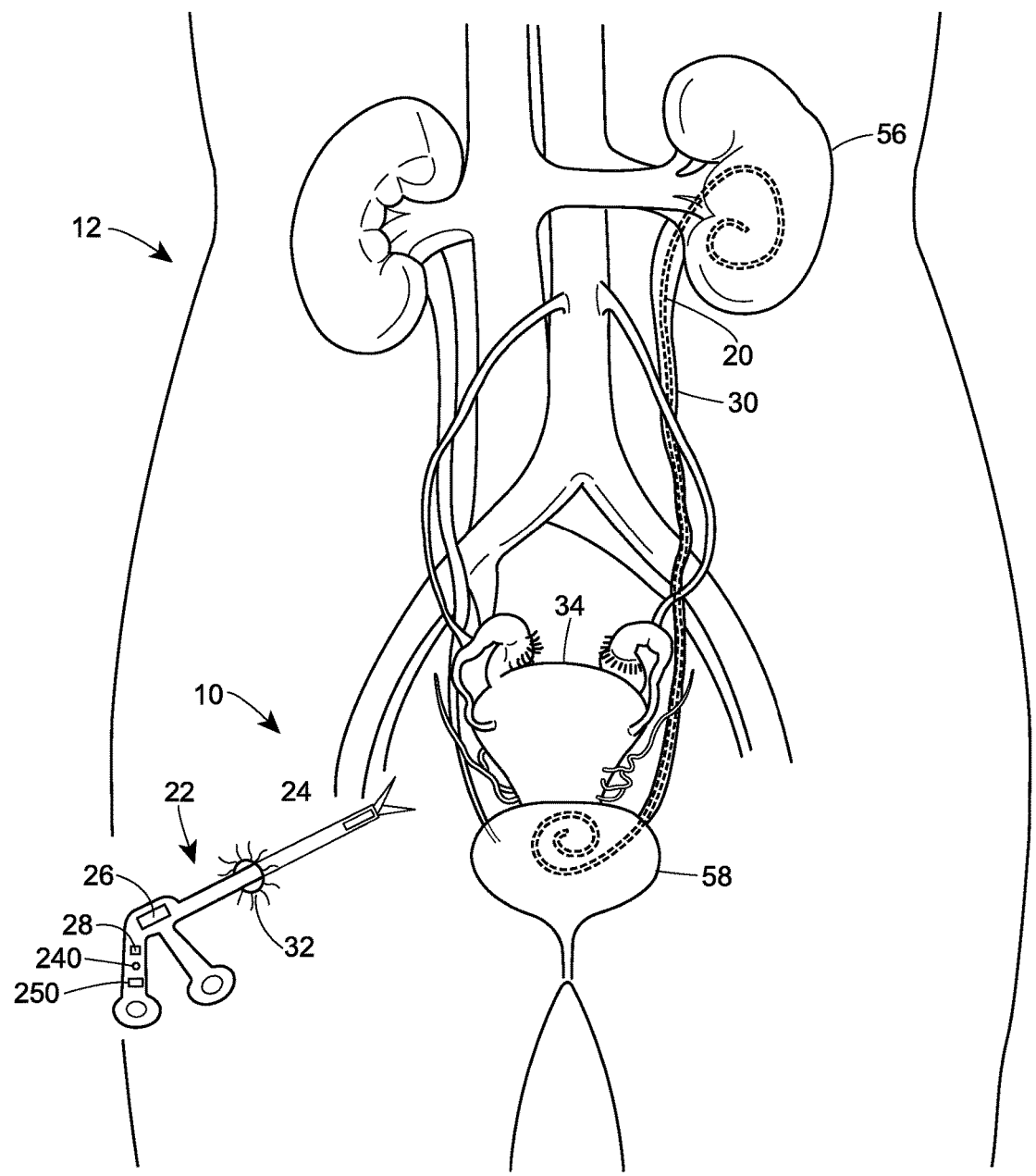
FIG. 1 is a schematic view of one embodiment of a surgical guidance system constructed in accordance with principles of the present disclosure.

FIG. 1 is a schematic representation of one embodiment of a surgical guidance system 10 used in a surgical procedure on a patient 12. In general, the surgical guidance system 10 includes an implantable device 20 configured to emit a detectable field having an intensity (e.g., a strength) that varies with distance, a surgical instrument 22, a proximity sensor 24 attached to the surgical instrument 22 and configured to detect the intensity of the detectable field, a control unit 26 configured to determine if the surgical instrument is within a predetermined distance of the implantable device 20, and a notification unit 28.

Generally, during a surgical procedure, the implantable device 20 is introduced into the patient 12 and attached to an anatomical structure (e.g., tissue, organ, vessel, etc.). In one embodiment, the implantable device 20 may be configured for attachment to a ureter 30 of the patient 12, as depicted in FIG. 1. The anatomical structure to which the implantable device 20 is attached may be a "non-target" anatomical structure in that the surgeon does not intend to resect or otherwise modify the anatomical structure during the surgical procedure. After implanting the implantable device 20, the surgeon may introduce the surgical instrument 22 through an incision 32 into the patient 12, and then maneuver and the surgical instrument 22 to treat, modify (e.g., cut, resect, etc.), repair, image, scan, measure, or otherwise interact with a target anatomical structure. In the embodiment illustrated in FIG. 1, the target anatomical structure is a uterus 34 of the patient 12. While maneuvering the surgical instrument 22, the surgeon may advance the surgical instrument 22 toward the non-target anatomical structure. As the surgical instrument 22 approaches the non-target anatomical structure, the proximity sensor 24 detects changes in the intensity of the detectable field emitted by the implantable device 20. If the intensity of the detectable field detected by the proximity sensor 24 is equal to or greater than a predetermined intensity level, the control unit 26 may determine that the surgical instrument 22 is within a predetermined distance of the implantable device 20, and subsequently control the notification unit 28 to notify (e.g., alert, warn, etc.) the surgeon of the proximity of the surgical instrument 22 to the non-target anatomical structure. As described below in more detail, the notification unit 28 may notify the surgeon through tactile feedback (e.g., vibrations), light, sound, graphics, text, and/or any other suitable notification method.

So configured, the surgical system 10 and basic surgical method of the present disclosure advantageously reduces the likelihood of unintentional injury to a non-target anatomical structure by notifying the surgeon of the proximity of the surgical instrument 22 to the non-target anatomical structure. In response to the notification, the surgeon can take appropriate measures to avoid or limit contact with the non-target anatomical structure. Since the surgical system 10 does not rely on visual identification of the non-target anatomical structure, the non-target anatomical structure can be located despite being obscured from view by, or visually indistinguishable from, other anatomical structures (e.g., fatty tissue, peritoneum, etc.) and/or bodily fluids (e.g., blood). Furthermore, since the surgical system 10 may not require complex and/or expensive imaging equipment to locate the non-target anatomical structure, the surgical system 10 may be relatively inexpensive. Also, a wide variety of conventional surgical instruments may be outfitted with the proximity sensor 24, the control unit 26, and/or the notification unit 28, with little or no modification to the surgical instrument. This renders the surgical system 10 suitable and economical for use in a wide variety of surgical procedures including, for example, hysterectomies, colorectal surgeries, myomectomies, among others.

Each of the foregoing components of the surgical guidance system 10 and the surgical methods of the present disclosure will now be described in more detail.

In general, the implantable device 20 marks (e.g., broadcasts) the location of an anatomical structure by emitting a detectable field. The intensity (e.g., strength) of the detectable field may vary with distance from the implantable device 20. In one embodiment, the intensity of the detectable field may generally decrease as one moves away from the implantable device 20, such that the intensity of the detectable field is inversely proportional to distance from the implantable device 20. The detectable field may be any energy-based field whose intensity can be measured by a sensor including, for example, a magnetic field, an electric field, an electromagnetic field, an sound field (e.g., an ultrasound field), a gravitational field, and/or radiation field, among others. The implantable device 20 may take any suitable form depending on the surgical procedure in which the implantable device 20 is to be used and/or the anatomical structure to be attached to the implantable device 20. The implantable device 20 may be configured as a stent, a wire mesh, a surgical clip, a surgical drape, a sterile fabric, a membrane, a prosthetic, a surgical tool (e.g., laparoscopic device, catheter, etc.), and/or any other medical device that may be used during a surgical procedure. In some embodiments, the implantable device 20 may be flexible so that the implantable device 20 can conform to the shape of the attached anatomical feature.

Figure 2:
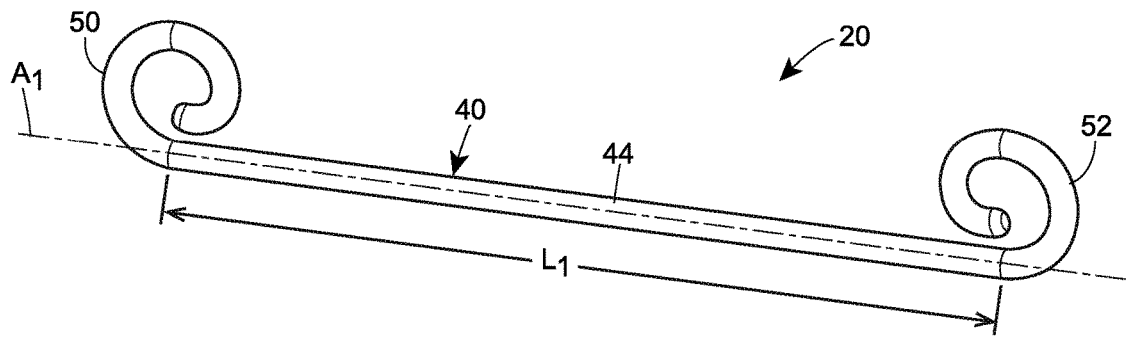
FIG. 2 is a perspective view of one embodiment of an implantable device constructed in accordance with principles of the present disclosure.
Figure 3:
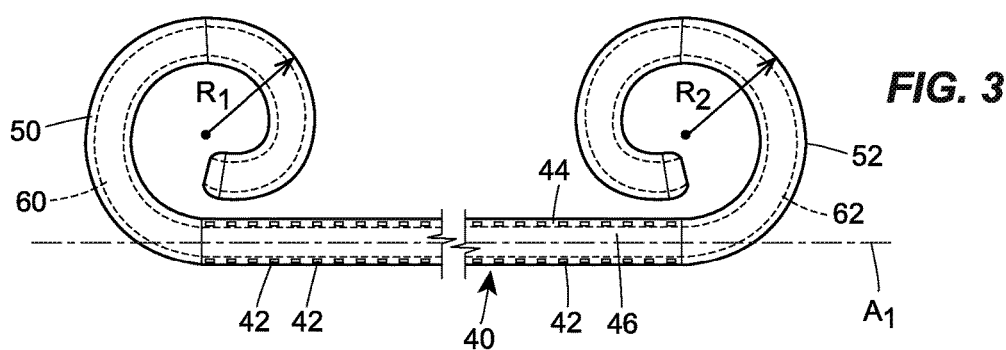
FIG. 3 is a cross-sectional view taken along a plane parallel to the longitudinal axis $A_1$ of the implantable device of FIG. 2.

FIG. 2 illustrates one embodiment of the implantable device 20 which is configured as a stent for attachment to a bodily lumen such as the ureter. The implantable device 20 may include a body 40 and a plurality of magnets 42 (see FIG. 3) that emit a magnetic field which surrounds the body 40. The strength of the magnetic field generally decreases as one moves away from the implantable device 20. The plurality of magnets 42 may function as a beacon that marks the location of the bodily lumen to which the implantable device 20 is attached. The plurality of magnets 42 may be embedded in the body 40 of the implantable device 20 as seen in FIG. 3. Additionally, or alternatively, the magnets 42 may be attached to an exterior surface of the body 40 and/or an interior surface of the body 40.

The body 40 may include a tubular member 44 that extends linearly along a longitudinal axis $A_1$ in a non-deformed state. In general, the tubular member 44 may be dimensioned so that it can be inserted through and/or disposed within the ureter. The tubular member 44 may be cylindrical and have a length $L_1$ along its longitudinal axis $A_1$ that is within a range between approximately (e.g., ±10%) 15.0-40.0 cm, or 22.0-32.0 cm, or 26.0-28.0 cm, or lesser or greater. The tubular member 44 may be hollow and thus define an inner lumen 46. In some embodiments, the inner lumen 46 may allow bodily fluids to pass through the implantable device 20 so that that implantable device 20 does not impact the physiological function of the attached anatomical structure. In some embodiments, the tubular member 44 may have two or more inner lumens. In other embodiments the tubular member 44 may be solid, and thus not have any inner lumens.

Figure 4:
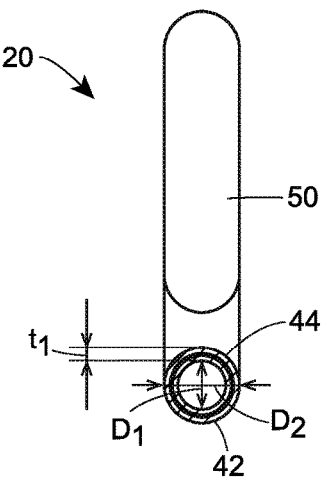
FIG. 4 is a cross-sectional view taken along line A-A of FIG. 3.

Referring to FIG. 4, an inner diameter $D_1$ of the tubular member 44, which corresponds to a diameter of the inner lumen 46, may be within a range between approximately (e.g., ±10%) 5.0-20.0 mm, or 10.5-17.4 mm, or 13.0-15.0 mm, or lesser or greater. An outer diameter $D_2$ of the tubular member 44 may be within a range between approximately (e.g., ±10%) 10.0-25.0 mm, or 14.1-21.0 mm, or 16.0-18.0 mm, or lesser or greater. In one embodiment, a wall thickness $t_1$ of the tubular member 44 may be approximately (e.g., ±10%) 3.6 mm, or lesser or greater.

In a natural, non-deformed state, the tubular member 44 may be linear as illustrated in FIG. 2. When implanted in an anatomical structure, the tubular member 4 may bend to conform to the shape of the anatomical structure. In some embodiments, the tubular member 44 may bend up to about approximately (e.g., ±10%) 8.0 degrees when implanted in the anatomical structure. In alternative embodiments, the tubular member 44 may be manufactured to possess an intrinsic curvature so that the tubular member 44 is curved in its natural, non-deformed state. An intrinsic curvature may facilitate placement of the tubular member 44 in a curved anatomical structure. The intrinsic curvature may be within a range between approximately (e.g., ±10%) 1.0-10.0 degrees, or 2.0-8.0 degrees, or 4.0-6.0 degrees, or lesser or greater.

Referring still to FIGS. 2-4, the body 40 of the implantable device 20 may include a first coiled member 50 and a second coiled member 52 positioned at opposite ends of the tubular member 44. The first and second coiled members 50, 52 may function to anchor the implantable device 20 at a desired position within the patient. Each of the first and second coiled members 50, 52 may curl back on itself in a shape that resembles a pigtail. The first coiled member 50 may have a radius $R_1$ and the second coil member 52 may have a radius $R_2$. In some embodiments, each of the first and second radii $R_1$, $R_2$ may be approximately (e.g., ±10%) 8.0 mm, or lesser or greater. The first coiled member 50 may be dimensioned to fit inside a first hollow anatomical structure (e.g., a kidney 56 as seen in FIG. 1), and the second coiled member 50 may be dimensioned to fit inside a second hollow anatomical structure (e.g., a bladder 58 as depicted in FIG. 1).

Figure 6:
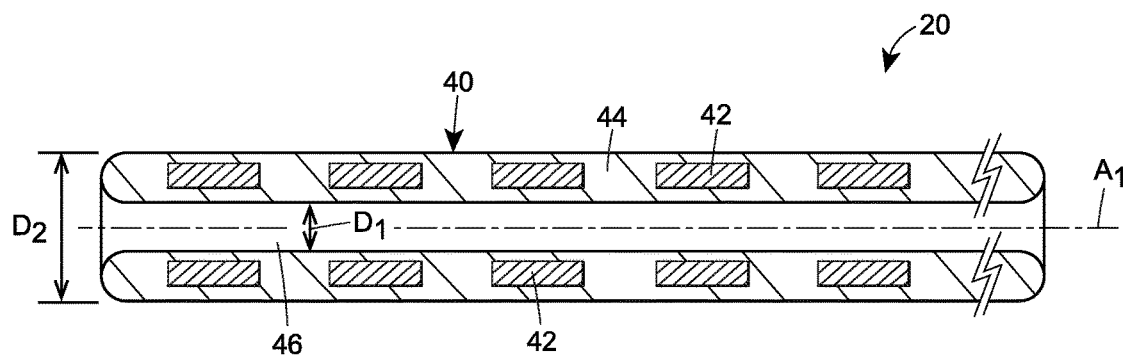
FIG. 6 is a cross-sectional view of one embodiment of an implantable device constructed in accordance with principles of the present disclosure.

The first coiled member 50 may include an inner lumen 60 in fluid communication with the inner lumen 46 of the tubular member 44, and the second coiled member may include an inner lumen 62 in fluid communication with the inner lumen 46 of the tubular member 44. In some embodiments, an inner diameter, an outer diameter, and a thickness of the first and second coiled member 50, 52 may have the same dimensions, respectively, as the inner diameter $D_1$, the outer diameter $D_2$, and the thickness $t_1$ of the tubular member 44. In some embodiments, the tubular member 44 and the first and second coiled members 50, 52 are integrally formed in one-piece and made of the same material. In alternative embodiments, the first and second coiled members 50, 52 may be separate from the tubular member 44 and removably attached to the tubular member 44. In still further alternative embodiments, the body 40 may not include the first and second coil members 50, 52, as shown in FIG. 6.

During insertion into the patient, a guidewire may be passed through the inner lumen 46 of the tubular member 42, the inner lumen 60 of the first coiled member 50, and the inner lumen 62 of the second coiled member 62. As such, the first and second coiled member 50, 52 may be substantially linear and not possess their pigtail shape. After the first and second coiled members 50, 52 are inserted into their respective hollow anatomical structures and the guidewire is removed, the first and second coiled members 50, 52 may curl back on themselves and assume their pigtail configurations, as illustrated in FIG. 1.

The body 40 of the implantable device 20, including the tubular member 44 and the first and second coiled members 50, 52, may be made of any biocompatible material and/or film such as polyethylene, polyester, polyurethane, silicone, liquid-silicone based resin, nylon, polyvinyl chloride (PVC), polyethylene terephthalate (PET), a metal alloy, titanium, or any combination thereof, or any other suitable material. Also, the material used for the body 40 may be synthetic and/or natural. Any suitable manufacturing technique including, for example, blow molding, heat shrinking, extrusion, and/or casting may be used to make the body 40. The body 40 of the implantable device 20 may include a structural reinforcement (not illustrated), such as a metallic or polymer coil(s) or strip(s), to impart the entire body 40, or a limited portion of the body 40, with a desired strength or flexibility. The exterior surface of the body 40 may be coated with a therapeutic agent (e.g., heparin, to inhibit encrustation), a hydrophilic coating (e.g., to facilitate advancement and/or sliding of the body 40 through a bodily lumen by forming a water saturated surface), and/or any other suitable coating.

The body 40 may be made of a flexible material so that it can bend to conform to the shape of an anatomical structure and/or to facilitate insertion into the patient. In some embodiments, the durometer of the body 40, and/or the durometer of the entire implantable device 20, may be within a range between approximately (e.g., ±10%) 10-70 Shore A, or 20-50 Shore A, or 24-47 Shore A, or lesser or greater, in accordance with ASTM D-2240.

While the present embodiment of the implantable device 20 has a body 40 that is configured as a stent, alternative embodiments could be configured differently, e.g., with the body 40 configured as a membrane or mesh that is placed over an area in a surgical site, or with the body 40 configured as configured as a surgical clip that grasps or clamps an anatomical structure, or with the body 40 configured as a surgical tool such as a laparoscopic device or a catheter.

Figure 5:
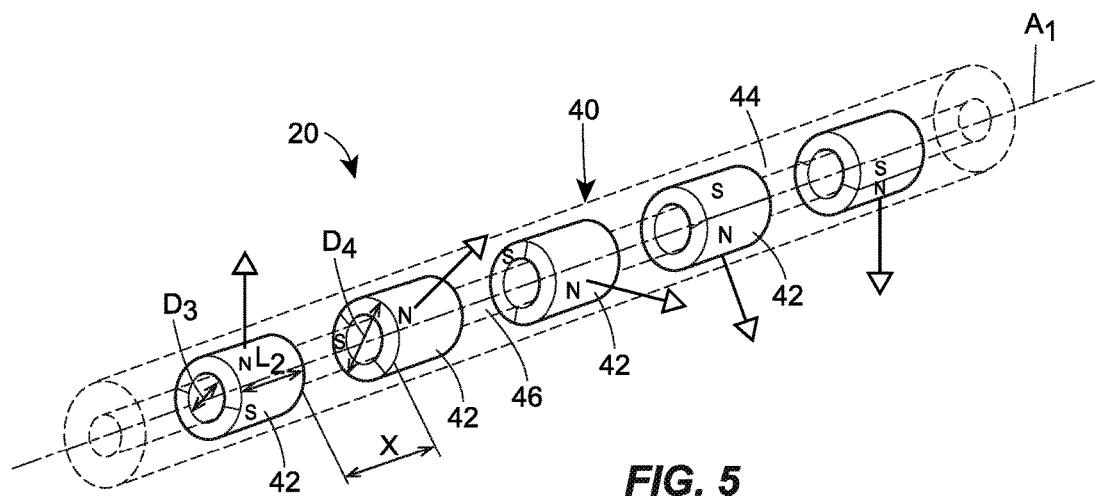
FIG. 5 is perspective view of one embodiment of an implantable device constructed in accordance with principles of the present disclosure.

Referring to FIG. 5, illustrated is one possible configuration of the magnets 42 of the implantable device 20. Each of the magnets 42 is tubular (e.g., ring-shaped, shaped like a hollow cylinder, etc.) and therefore may possess an inner diameter $D_3$ and an outer diameter $D_4$. The inner diameter $D_3$ may be in a range between approximately (e.g., ±10%) 0.05-1.10 mm, or 0.1-0.99 mm, or 0.40-0.60 mm, or lesser or greater. The outer diameter $D_4$ may be in a range between approximately (e.g., ±10%) 1.00-2.00 mm, or 1.16-1.93 mm, or 1.4-1.6 mm, or lesser or greater. The length $L_2$ of each of the magnets 42 may be in a range between approximately (e.g., ±10%) 0.20-2.0 mm, or 0.48-1.98 mm, or 0.80-1.20 mm. The tubular shape of the magnets 42 may facilitate the passage of a bodily fluid through the implantable device 20. In alternative embodiments (not illustrated), such as an embodiment where the body 40 of the implantable device 20 is solid, the magnets 42 may be solid and/or have the shape of a disc.

Each of the magnets 42 may be embedded entirely within the tubular member 44, as illustrated in FIG. 5. In alternative embodiments, the magnets 42 may be partially embedded within the tubular member 44 so that the magnets protrude outwardly and/or inwardly away from the tubular member 44. In other embodiments, the magnets 42 may be attached to an exterior surface of the tubular member 44 or attached to an interior surface of the tubular member 44. In other embodiments, the magnets 42 may replace cross-sectional segments of the tubular member 44 at regular intervals.

Each of the magnets 42 may be arranged adjacent one another and parallel to the longitudinal axis $A_1$ of the tubular member 44 of the body 40, as illustrated in FIG. 5. In one embodiment, each of the magnets 42 may be spaced apart from an adjacent one of the magnets 42 by a distance X, as shown in FIG. 5, such that the magnets are arranged at spaced apart intervals. The distance X may be in a range between approximately (e.g., ±10%) 5.0-20.0 mm, 8.0-17.0 mm, 10.0-15.0 mm, 11.5-13.5 mm, or lesser or greater. In one embodiment, the distance X may be equal to approximately (e.g., ±10%) 12.0 mm, which, in some configurations, may be an optimal distance for creating a uniform magnetic field. In one embodiment, the distance X may be greater than or equal to approximately (e.g., ±10%) 8.0 mm. The spacing between the magnets 42 may allow the implantable device 20 to bend when inserted into the patient and conform to the shape of an anatomical structure to which the implantable device 20 is to be attached. Accordingly, the spacing between the magnets 42 imparts the implantable device 20 with a degree of flexibility.

In some embodiments (not illustrated), in addition to, or as an alternative to, being arranged at spaced apart intervals along the longitudinal axis $A_1$, the magnets may be arranged at spaced apart intervals around a circumference of the body 40 of the implantable device 20.

The magnets 42 may be made of any permanently or semi-permanently ferromagnetic material including, for example, iron, nickel, cobalt, rare earth metals, lodestone, and/or any other material capable of generating a persistent magnetic field.

Still referring to FIG. 5, each of the magnets 42 may emit its own individual magnetic field 70. The combination of the individual magnetic fields 70 may define a composite magnetic field which may be referred to as the magnetic field of the implantable device 20. The individual magnetic fields 70 each may be generally oriented in an outward radial direction that is perpendicular to the longitudinal axis $A_1$, as shown in FIG. 5. In other embodiments, some or all of the individual magnetic fields 70 may be generally oriented in an inward radial direction that is perpendicular to the longitudinal axis $A_1$. In some embodiments, some or all of the individual magnetic fields 70 generally oriented in a direction that is parallel to the longitudinal axis $A_1$.

Figures 7, 8:
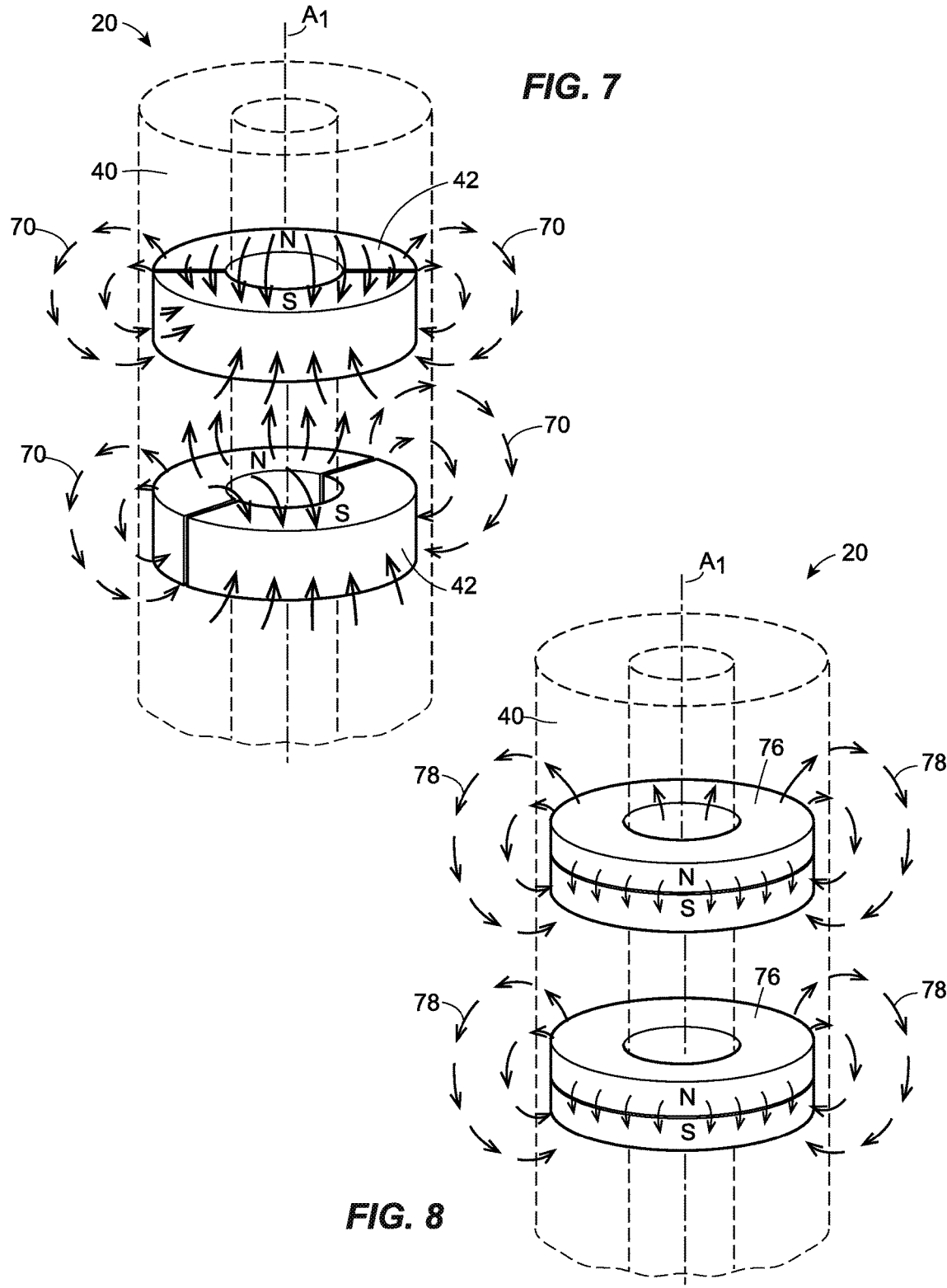
FIG. 7 is a perspective view of one embodiment of a diametrically-magnetized implantable device constructed in accordance with principles of the present disclosure.
FIG. 8 is a perspective view of one embodiment of an axially-magnetized implantable device constructed in accordance with principles of the present disclosure.

Each of the magnets 42 possesses a north pole N and a south pole S. In the embodiment illustrated in FIG. 5, the north pole N and the south pole S of each magnet 42 may be arranged at diametrically opposite ends of the magnet 42. FIG. 7 illustrates an enlarged view of this configuration of the magnets 42 and its associated magnet field 70. Additionally, as depicted in FIGS. 5 and 7, the poles of each magnet 42 may be rotationally offset from the poles of an adjacent one of the magnets 42, such that the rotational position of the poles of the magnets 42 changes along the longitudinal axis A1. As illustrated in FIG. 5, the rotational position of the poles may change at regular intervals along the longitudinal axis $A_1$. In one embodiment, the intervals may be in a range between approximately (e.g., ±10%) 2-15 degrees, or 3-10 degrees, or 5-7 degrees, or lesser or greater. For example, a first one of the magnets 42 may have a north pole N located at a first rotational position, a second one of the magnets 42 immediately adjacent to the first one of the magnets 42 may have a north pole N located at a second rotational position rotationally offset from the first rotational position by approximately (e.g., ±10%) 5 degrees, a third one of the magnets 42 immediately adjacent to the second one of the magnets 42 may have a north pole N located at a third rotational position rotationally offset from the first rotational position by approximately (e.g., ±10%) 10 degrees, and so forth. By having the poles of adjacent magnets 42 being rotationally offset, a more uniform overall magnetic field may be created for the implantable device 20.

Figure 9:
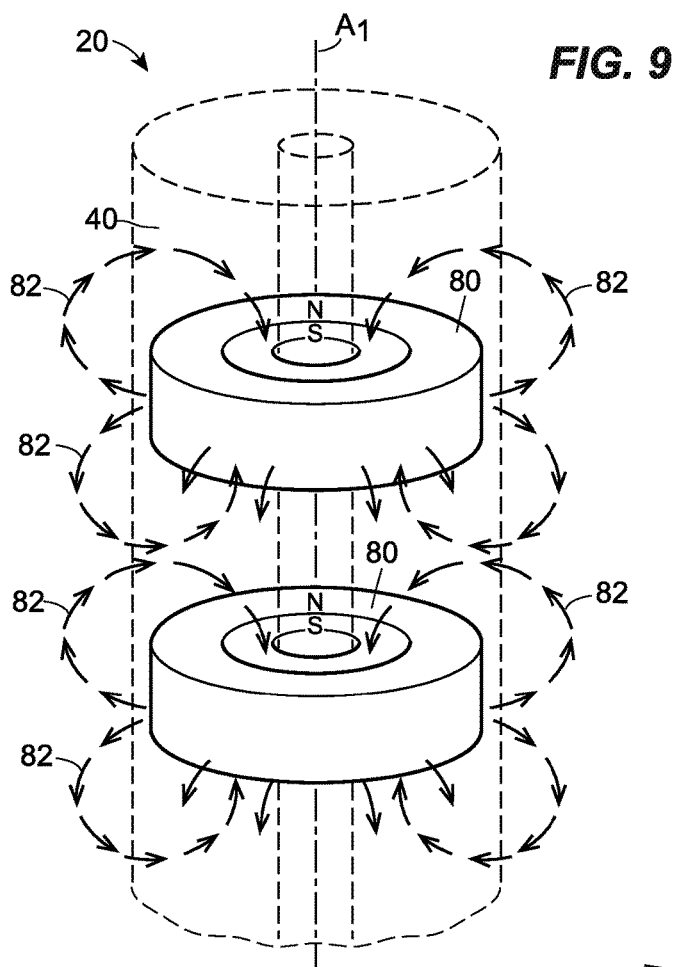
FIG. 9 is a perspective view of one embodiment of an radially-magnetized implantable device constructed in accordance with principles of the present disclosure.

Other configurations of the north pole N and the south pole S are also envisioned. FIG. 8 illustrates magnets 76 which each have a north pole N and south pole S are arranged at axially opposite ends of the magnet 76 and a magnetic field 78. FIG. 9 depicts magnets 80 which each have a north pole N and south pole S are arranged concentrically (e.g., coaxially), with the south pole S being located radially inward of the north pole N. The magnetic field 82 associated with this configuration is also depicted in FIG. 9. In other embodiments, the magnets may be configured as one or more magnetic wires or coils that generate a magnetic field with a polarity that is parallel to the longitudinal axis $A_1$. In other embodiments, instead of being arranged along a single axis, the magnets may be arranged in a grid, and incorporated into, for example, a mesh.

As discussed above, the detectable field of the implantable device 20 may have an intensity that decreases as one moves away from the implantable device 20. Accordingly, the intensity of the detectable field may vary inversely with distance from the implantable device. In one embodiment, the intensity of a magnetic field at the exterior surface of the implantable device 20 may be in a range between approximately (e.g., ±10%) 800-2200 Gauss, or lesser or greater. At a distance of 2.0 cm away from the implantable device 20, the intensity of the magnetic field may be in a range between approximately (e.g., ±10%) 300-650 Gauss, or lesser or greater. At a distance of 4.0 cm away from the implantable device 20, the intensity of the magnetic field may be in a range between approximately (e.g., ±10%) 180-550 Gauss, or lesser or greater. Accordingly, by detecting the intensity of the magnetic field with a sensor, one may be able to determine the distance between the sensor and the implantable device 20.

Figure 10:
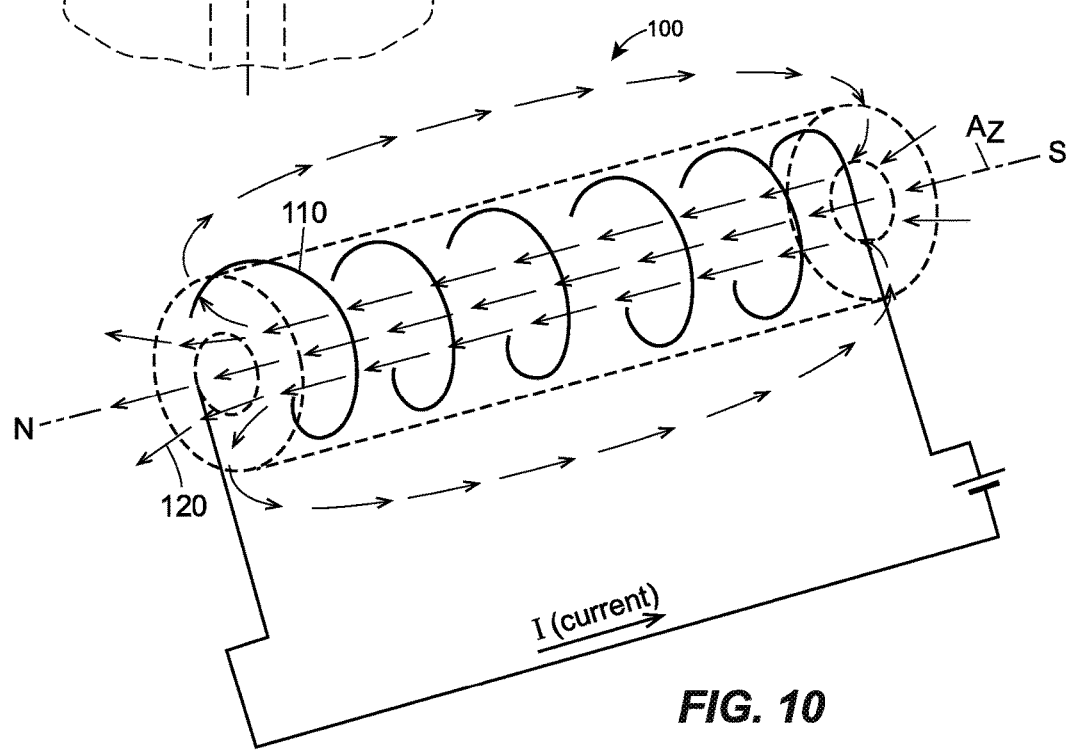
FIG. 10 is a perspective view of one embodiment of a current-carrying implantable device constructed in accordance with principles of the present disclosure.

While the foregoing embodiments of the implantable device utilize magnets to create the magnet field, alternative embodiments may employ different means to generate the magnetic field, or generate a different type of detectable field. FIG. 10 illustrates an implantable device 100 having a current-carrying wire 110 to generate a magnetic field 120. The current-carrying wire 110 depicted in FIG. 10 is coiled around the exterior surface of a body of the implantable device 100. In other embodiments, the current-carrying wire 110 may be coiled around an interior surface of the body of the implantable device 100, and/or embedded within the body of the implantable device 100. Suitable materials for the current-carrying wire 110 include copper, aluminum, iron, silver, gold, platinum, brass, bronze, tungsten, or any combination thereof, and/or any other conductive material. The current-carrying wire 110 may or may not be insulated, and may be attached to any device capable of generating a current through the current-carrying wire 110. In the illustrated embodiment, the magnetic field 120 is generated circumferentially to a cross-section of the implantable device 100. Alternative embodiments may utilize multiple current-carrying wires arranged parallel to a longitudinal axis $A_2$ of the implantable device 100.

The current-carrying wire allows a surgeon to adjust the size and/or shape of the magnetic field so that it minimally intersects with other surgical devices and/or anatomical structures, thereby minimizing the effects of interference.

Figure 11:
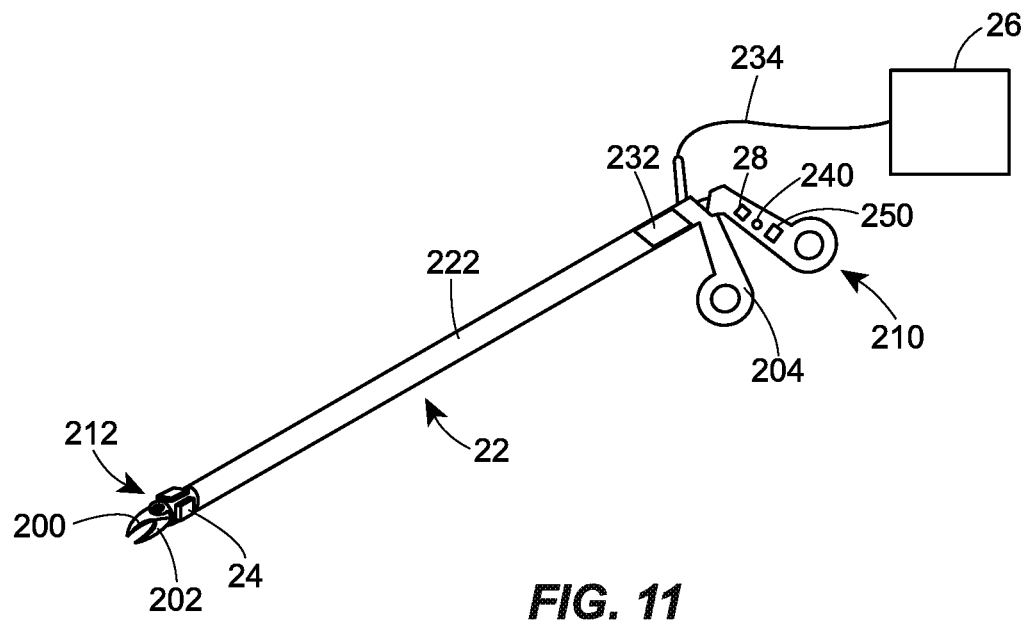
FIG. 11 is a perspective view of one embodiment of a surgical instrument constructed in accordance with principles of the present disclosure.

Turning to FIG. 11, illustrated is an embodiment of the surgical instrument 22. Here, the surgical instrument 22 is configured as a laparoscopic grasper and therefore includes pair of grasping members 200, 202 (i.e., a surgical tool) attached to the distal end 212 of the surgical instrument 22 which can be manually actuated by a surgeon via a handle unit 204. However, the surgical instrument 22 is not limited to being laparoscopic grasper, and could be any surgical instrument capable of being introduced into a patient to treat, modify (e.g., cut, resect, etc.), image, scan, measure, or otherwise interact with one or more anatomical structures. As an addition to, or as an alternative to the grasping members 200, 202, the surgical tool attached to the distal end 212 of the surgical instrument 22 may include any one of, or any combination of: scissors, calipers, forceps, an occluder, a clamp, a retractor, a distractor, a scalpel, a lancet, a drill, a drill bit, rasps, trocars, a harmonic scalpel, rongeurs, a dilator, a specula, a suction tube, a stapler, a needle, a probe, an endoscope, a mechanical cuter, an ultrasonic cutter, a laser cutter, and/or any other suitable surgical tool. In some embodiments, the surgical instrument 22 may be configured as laparoscopic scissors, laparoscopic dissectors, a laparoscopic monopolar cautery, a laparoscopic bipolar cautery, a colpotomizer, a surgical manipulator, a robotic surgical instrument (e.g., a computer-controlled surgical instrument), and/or any other medical device.

Additionally, the surgical instrument 22 is not limited to surgical instruments that are used to treat the human body, and could be surgical instruments that are used to treat animals such a livestock, dogs, cats, fish, etc.

Figure 12:
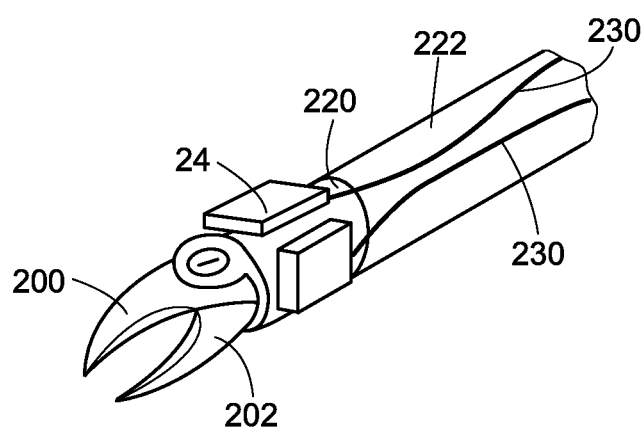
FIG. 12 is an enlarged view of Section A of FIG. 11.

The surgical instrument 22 may have a proximal end 210 and a distal end 212. During a surgical procedure, the distal end 212 of the surgical instrument 22 may be inserted inside the patient while the proximal end 210 of the surgical instrument 22 remains exterior to the patient, as illustrated in FIG. 11. The grasping member 200, 202, or other surgical mechanism or tool, may be attached to the distal-most portion (i.e., the tip) of the distal end 212, whereas the handle unit 204 may attached to the proximal-most portion of the proximal end 210, as depicted in FIG. 12. The handle unit 204 may be held in the hand of a surgeon during the surgical procedure and manually actuated by the surgeon to cause the grasping members 200, 202 to clamp and release an anatomical structure of interest.

Referring to FIG. 12, the proximity sensor 24 may be attached to the distal end 212 of the surgical instrument 22 proximal to the grasping members 200, 202. The proximity sensor 24 may be any sensor capable of detecting changes in the intensity of an energy-based field (e.g., a magnetic field, an electric field, an electromagnetic field, an acoustic field, a gravitational field, a radiation field, etc.). In one embodiment, the proximity sensor 24 is a three-axis Hall effect sensor configured to detect an intensity of a magnetic field in three independent directions including an x-direction, a y-direction, and a z-direction. In other embodiments, the proximity sensor 24 may be a two-axis Hall effect sensor configured to detect an intensity of a magnetic field in two independent directions. In other embodiments, the proximity sensor 24 may be a single-axis Hall effect sensor configured to detect an intensity of a magnetic field in a single direction. In other embodiments, the proximity sensor 24 may utilize mechanisms different from Hall effect sensing for detecting changes in the intensity of the magnetic field emitted by the implantable device 20, including, but not limited to: magneto-diode, magneto-transistor, magneto-resistance magnetometer, magnetic tunnel junction magnetometer, microelectromechanical systems sensor variations, nuclear precession magnetic field sensing, optical pumping, fluxgate magnetometer, search coil sensor, superconducting quantum interface device (SQUID) magnetometer, and/or spin exchange relaxation-free (SERF) magnetometer.

As illustrated in FIG. 12, the proximity sensor 24 may be removably attached to the distal end 212 of the surgical instrument 22 by a clip 220. The clip 220 makes it feasible to outfit an existing surgical instrument 22 with the proximity sensor 24 without having to re-design the existing surgical instrument 22. The clip 220 may be a circular or semi-circular sleeve that slips over and/or grasps a distal end of an elongate cylindrical portion 222 of the surgical instrument 22. In some embodiments, the clip 220 may utilized spring-loaded mechanism to grasp onto the surgical instrument 22. Alternatively, or additionally, an adhesive may be used for mounting the clip 220 on the surgical instrument 22. The clip 220 may be configured to hold the proximity sensor 24 onto the surgical instrument 22 for the duration of a surgical procedure, after which the clip 220 may be removed, if so desired. The clip 220 may be made of any suitable material including plastic, metal, or any combination thereof. In some embodiments, the clip 220 may be configured to permanently attach the proximity sensor 24 to the surgical instrument 22. In some embodiments, the clip 220 may be omitted, and the proximity sensor 24 may be built into the surgical instrument 22 and/or integrally formed in one-piece with the surgical instrument 22.

Still referring to FIGS. 11 and 12, the proximity sensor 24 may be connected to, and in communication with, the control unit 26 via wires 230, circuit 232, and wire 234. The wires 230 may extend between the proximity sensor 24 and the circuit 232, and the wire 234 may extend between the circuit 232 and the control unit 26. The wires 230 and/or the wire 234 may be electrically-insulated to protect the patient and/or the surgeon from electric shock. The circuit 232 and the wire 234 may allow the control unit 26 to be removably attached to the surgical instrument 22, and to be positioned remote from the surgical instrument 22. In other embodiments, such as the one illustrated in FIG. 1, the circuit 232 and the wire 234 may be omitted and the control unit 26 may be mounted directly on the surgical instrument 22.

In some embodiments, the sensitivity of the proximity sensor 24 to the detectable field may be adjusted by a sensitivity knob or toggle 240 protruding from the handle unit 204. The sensitivity knob or toggle 240 advantageously may allow the surgeon to increase the sensitivity of the proximity sensor 24 if it is failing to detect the detectable field, or decrease the sensitivity of the proximity sensor 24 if it is experiencing a high degree of interference from external sources (e.g., the earth's magnetic field, other medical devices, etc.).

In some embodiments, a reference sensor 250 may be attached to the handle unit 204. The reference sensor 250 may be used to detect the intensity of a background field (e.g., the magnetic field of the earth) so that the intensity of the background field can be subtracted from the measurement made by the proximity sensor 24. This may allow the control unit 26 to more accurately determine the intensity of the detectable field detected by the proximity sensor 24, and therefore better predict whether the distal end 212 of the surgical instrument 22 is near the implantable device 20.

Referring to FIG. 12, the notification unit 28 may be attached to the handle unit 204 of the surgical instrument 22. In alternative embodiments, the notification unit 28 may be separate and spaced apart and remote from the surgical instrument 22. The notification unit 28 may be connected to, and in communication with, the control unit 26 via wires (not shown). The control unit 26 may control the notification unit 28 to provide a notification to the surgeon, or other user of the surgical instrument 22, that the distal end 212 of the surgical instrument 22 is near and/or in danger of contacting the implantable device 20. The notification unit 28 may include a vibration mechanism driven by a controllable electric motor, a light (e.g., an LED), a display (e.g., a touchscreen), a speaker, a buzzer, or any combination thereof, and/or any other means for communicating information to a person. The notification generated by the notification unit 28 may take the form of a vibration generated in the handle unit 205 which can be felt by the operator of the surgical instrument, a flashing light, a colored light such as red light, an audible alarm, a graphic displayed on a screen, text displayed on a screen, or any combination thereof, and/or any other form of communication.

Figure 13:
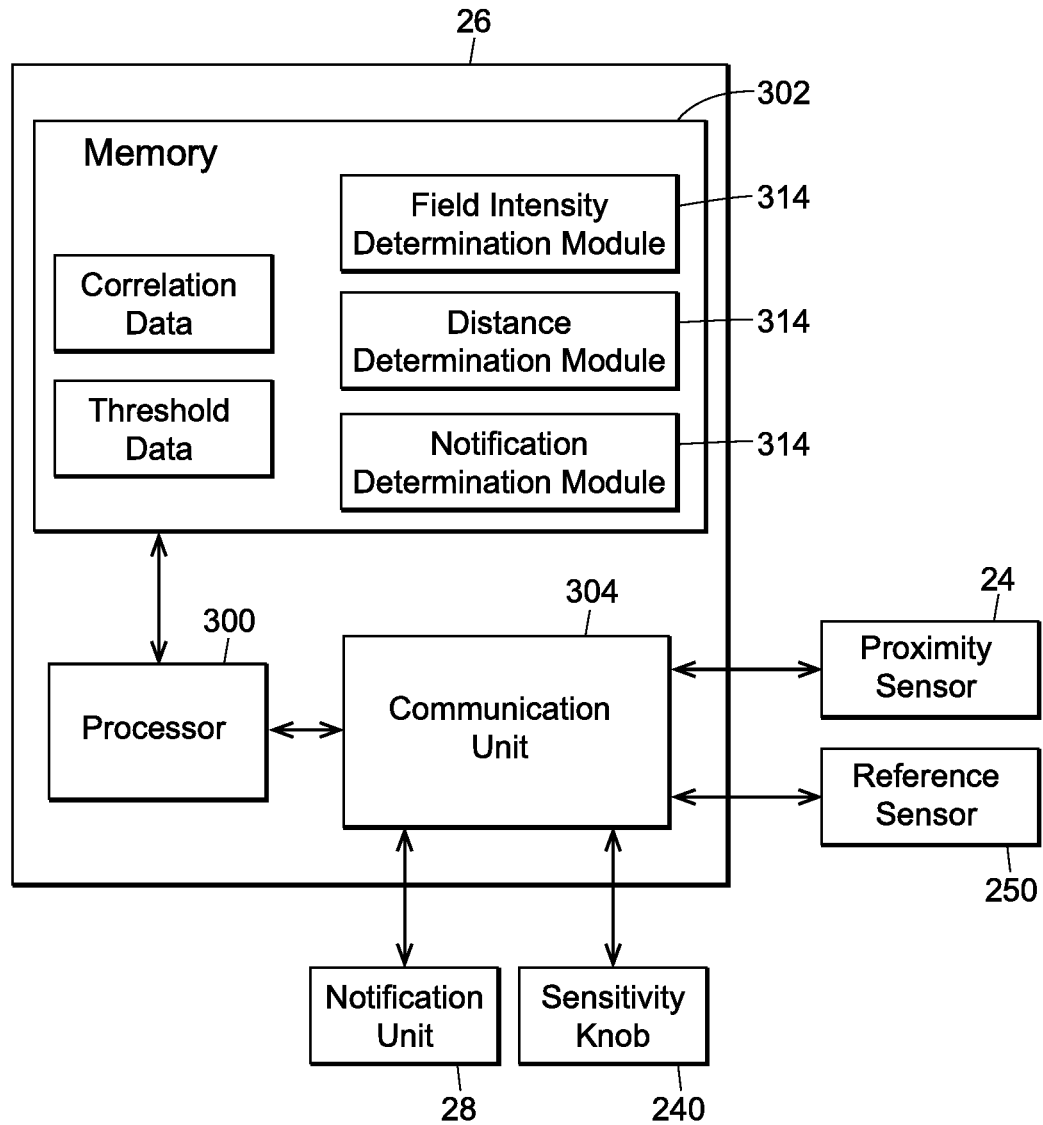
FIG. 13 is a block diagram of one embodiment of a control unit constructed in accordance with principles of the present disclosure.

FIG. 13 depicts a block diagram of one possible configuration of the control unit 26. The control unit 26 may include a processor 300 (e.g., a microprocessor), a memory 302 (e.g., a random access memory (RAM), a non-volatile memory such as a hard disk, a flash memory, a removable memory, a non-removable memory, etc.), and a communication unit 304. The elements of the control unit 26 may communicate with each other via a system bus (not illustrated). The processor 300, the memory 302, and the communication unit 304 may be discrete components or incorporated into a single component. The processing unit 300 may be configured to fetch and execute non-transitory computer-readable instructions stored in the memory 302 to control the operation of, for example, the sensor 24, the notification unit 28, the sensitivity knob 240, the reference sensor 250, and/or other electric components of the surgical instrument 22. The communication unit 304 may transmit and receive signals with: the sensor 24, notification unit 28, the sensitivity knob 240, the reference sensor 250, and/or an external computer (not illustrated).

In some embodiments, the memory 302 may store correlation data 310, threshold data 312, a field intensity determination module 314, a distance determine module 316, and a notification module 318. The correlation data 310 may include a table, or other data structure, of various input signals from the sensor 24 and corresponding intensities of the detectable field. In addition, the correlation data 310 may include a table, or other data structure, of various distances between the sensor 24 and the implantable device 22 and corresponding intensities of the detectable field. Since the sensor 24 is attached to the distal end 212 of the surgical instrument 22, the distances included in the correlation data 310 may correspond to distances existing between the distal end 212 of the surgical instrument 22 and the implantable device 22.

The threshold data 312 may include a recommended or required minimum distance to be maintained between the distal end 212 of the surgical instrument 22 and the implantable device 20 in order to avoid injury to the anatomical object to which the implantable device 20 is attached. This minimum distance may be a predetermined distance in the sense that it may be determined before the surgical procedure starts and/or during the surgical procedure. For example, the surgeon may set the minimum distance before and/or during the surgical procedure. The minimum or predetermined distance may be a discrete distance (e.g., 0.5 cm, 1.0 cm, 1.5 cm, 2.0 cm, 2.5 cm, 3.0 cm, 3.5 cm, or 5.0 cm, etc.) or a distance range (e.g., 0.5-1.0 cm, 1.0 cm-2.0 cm, or 2.0 cm-5.0 cm, etc.). Alternatively, or additionally, the threshold data 312 may include a threshold intensity that corresponds to a minimum intensity of the detectable field expected to be detected by the sensor 24 when the distal end 212 of the surgical instrument 22 is within a minimum distance of the implantable device 20.

The field intensity determination module 314 may include a set of instructions stored in the memory 302, which, when executed by the processor 300, cause the processor 300 to receive an input signal from the sensor 24 and compare the input signal with the correlation data 310 to determine an intensity of the detectable field at the current location of the sensor 24. In some embodiments, this process may involve the processor 300 initially subtracting an input signal from the reference sensor 250 from the input signal from the sensor 24, and the comparing the result to the correlation data 310, in order to account for a background field such as the earth's magnetic field.

The distance determination module 316 may include a set of instructions stored in the memory 302, which, when executed by the processor 300, cause the processor 300 to compare the field intensity determined by the field intensity determination module 314 with the correlation data 310 to determine the current distance between distal end 212 of the surgical instrument 22 and the implantable device 20.

The notification module 318 may include a set of instructions stored in the memory 302, which, when executed by the processor 300, cause the processor 300 to compare the current distance between the distal end 212 of the surgical instrument 22 and the implantable device 20 with the threshold data 312 to determine if the distal end 212 of the surgical instrument 22 is within the predetermined distance of the implantable device 20. This comparison may involve determining whether current distance between the distal end 212 of the surgical instrument 22 and the implantable device 20 is less than or equal to the predetermined distance stored in the threshold data 312. If so, the notification module 318 may cause the processor 300 to output a control signal that activates the notification unit 28. By activating the notification unit 28, the notification unit 28 may, for example, generate vibrations, emit light, display a warning graphic or text, sound an alarm or buzzer, or any combination thereof.

In some embodiments, the intermediate step of using the distance determination module 316 to determine the current distance between the distal end 212 of the surgical instrument 22 and the implantable device 20 may be omitted. Instead, the notification module 318 may compare the intensity of the detectable field determined by the field intensity determination module 314 with the threshold intensity stored in the threshold data 312, and, if the intensity of the detectable field determined by the field intensity determination module 314 is greater than or equal to the threshold intensity, the notification module 318 may cause the processor 300 to output a control signal that activates the notification unit 28.

While the foregoing embodiment of the control unit 26 may utilize a combination of hardware and software to determine if the distal end 212 of the surgical instrument 22 is within a predetermined distance of the implantable device 20 and output a control signal for activating the notification unit 28, alternative embodiments of the control unit 26 can be arranged differently, for example, with the control unit 26 only utilizing hardware (no software) to determine if the distal end 212 of the surgical instrument 22 is within a predetermined distance of the implantable device 20 and output a control signal for activating the notification unit 28.

In some embodiments, in addition to the proximity sensor 24, a pressure sensor (not illustrated) may be attached to the distal end 212 of the surgical instrument 22, and may be configured to detect whether the distal end 212 of the surgical instrument 22 has contacted an object. In such embodiments, the pressure sensor may be used as a backup sensor in the event that the proximity sensor 24 fails to detect, or improperly detect, the detectable field emitted by the implantable device 20.

In alternative embodiments of the surgical guidance system, rather than mounting the proximity sensor on the surgical instrument and configuring the implantable device to emit the detectable field, a reverse configuration may be used. That is, the proximity sensor may be incorporated into the implantable device and the detectable field generator may be attached to the distal end of the surgical instrument. Such an embodiment may function the same, and include the same components, as the surgical guidance system 10 discussed above, except that the locations of the proximity sensor and the detectable field generator are switched.

A surgical method (e.g., operation) of using the surgical system 10 will now be described with reference to FIG. 1. While the uterus 34 and the ureter 30 of the patient 12 are, respectively, the target and non-target anatomical structures of the surgical method described below, the target and non-target anatomical structures may be any anatomical structure including the stomach, the heart, the intestines, the lungs, the esophagus, an artery, a vein, or any other tissue, organ, vessel, or cellular structure, or even a single cell. Also, while the following surgical method may be performed in whole, or in part, by a surgeon or another medically-trained individual, in other embodiments, some or all of the steps of the surgical method may be performed by a computer-controlled surgical robot.

Initially, a 22 French rigid cystoscope may be introduced into the patient through the urethra (not illustrated) and into the bladder 58. Next, a guidewire (not illustrated), under fluoroscopic vision, may be passed through the cystoscope, into and up through the ureter 30, and into the kidney 56.

Subsequently, the implantable device 20, which may be a 6 French by 26 cm right double-J magnetic ureteral stent, may introduced into the patient 12 by being passed over the guidewire. The implantable device 20 may be advanced into the patient 12 until the first coiled member 50 is positioned within the kidney 56 and the second coiled member 52 is positioned within the bladder 58. At this stage of the surgical method, the first and second coiled members 50, 52 may be substantially linear due to the guidewire. Subsequently, the guidewire may be removed from the patient, and the first and second coiled members 50, 52 may each curl and assume their pigtail shapes, as shown in FIG. 1. The curling the first and second coiled members 50, 52 may anchor opposite ends of the implantable device 20 in the kidney 56 and the bladder 58, and thereby attach the body 40 of the implantable device 20 in the ureter 30. In some embodiments, the tubular member 44 of the implantable device 20 may have an outer diameter $D_2$ that is equal to or slightly larger than the inner diameter of the ureter 30, such that a friction fit may exist between the tubular member 44 and the ureter 30. The implantable device 20 may be removably attached to the ureter 30 in that the implantable device 20 can be removed after the completion of the surgical operation.

Next, one or more incisions 32 may be formed in the abdomen of the patient 12. Then, the distal end 212 of the surgical instrument 22 may be introduced into the patient 12 through one of the incisions 32. The surgeon may advance the distal end 212 of the surgical instrument 22 toward the target anatomical structure, which may be the uterus 34, with the intention of treating, modifying (e.g., cutting, resecting, etc.), repairing, imaging, scanning, measuring, or otherwise interacting with the uterus 34. In doing so, the distal end 212 of the surgical instrument 22 may also be advanced toward the ureter 30 and/or the implantable device 20. During the treatment of the uterus 34, the distal end 212 of the surgical instrument 22 may be advanced toward and/or away from the ureter 30 and/or the implantable device 20.

Throughout the surgical operation, the proximity sensor 24, which is located at the distal end 212 of the surgical instrument 22, may be detect the intensity of the detectable field (e.g., a magnetic field) emitted by the implantable device 20. The control unit 26 may receive detection signals from the proximity sensor 24 and determine if the distal end 212 of the surgical instrument 22 is within a predetermined distance of the implantable device 20 by analyzing the detection signals. This determination may involve the execution of the field intensity determination module 314, the distance determination module 316, and/or the notification module 318 described above. If the proximity sensor 24 is unable to detect the detectable field, or if the proximity sensor 24 is experiencing interference, the surgeon may adjust the sensitivity knob 240 during the operation.

If the distal end 212 of the surgical instrument 22 is determined to be within the predetermined distance of the implantable device 20, the control unit 26 may output a control signal to the notification unit 28. In response, the notification unit 28 may notify (e.g., alert, warn, etc.) the surgeon by generating vibrations that can be felt in the handle unit 204, emitting light, displaying a warning graphic or text, sounding an alarm or buzzer, or any combination thereof. After receiving this notification, the surgeon may maneuver the distal end 212 of the surgical instrument 20 to avoid or limit contact with the ureter 30. This may involve ceasing the advancement of the distal end 212 of the surgical instrument 22 toward the implantable device 20 and/or the ureter 30. Finally, once treatment of the uterus 34 or other target anatomical structure is complete, the surgical instrument 22 and the implantable device 20 may be removed from the patient 12, and the incision 32 may be sutured shut.

In some embodiments, in response to the notification, rather than maneuver the surgical instrument 20 to avoid or limit contact with the ureter 30, the surgeon may continue advancing the distal end 212 of the surgical instrument 22 toward the implantable device 20 until the distal end 212 of the surgical instrument 22 contacts the ureter 30. Subsequently, the surgeon may use the surgical instrument 22 to treat, modify (e.g., cut, resect, etc.), image, scan, measure, or otherwise interact with the ureter 30. Accordingly, in some embodiments, the surgical guidance system may be used to help guide the surgeon to the anatomical structure attached to the implantable device.

Although the foregoing systems, devices, and methods have been described primarily in the context of treating the human body, the scope of the present disclosure is not limited to human applications. The foregoing systems, device, and methods may be implemented in surgical procedures, and other applications, that involve animals (e.g., livestock, dogs, cats, fish, etc.), insects, or any other living thing, or even non-living things.

While the present disclosure has been described with respect to certain embodiments, it will be understood that variations may be made thereto that are still within the scope of the appended claims.

What is claimed is:

1. A surgical guidance system comprising:
an implantable device configured for attachment to an anatomical structure and to emit a detectable field;
a surgical instrument having a proximal end and a distal end, the distal end of the surgical instrument defining a leading end of the surgical instrument during insertion into a patient and being movable relative to the implantable device while the implantable device is attached to the anatomical structure;
a surgical tool attached to the distal end of the surgical instrument, the surgical tool including one or more of: a laparoscopic grasper, scissors, calipers, forceps, a retractor, a scalpel, a lancet, rasps, a trocar, a harmonic scalpel, rongeurs, a dilator, a specula, a suction tube, a stapler, a needle, an ultrasonic cutter, a laser cutter, laparoscopic dissectors, a laparoscopic monopolar cautery, a laparoscopic bipolar cautery, and a colpotomizer;
a proximity sensor attached to the distal end of the surgical instrument and configured to detect the detectable field; and
a control unit in communication with the proximity sensor and configured to use the proximity sensor to determine if the distal end of the surgical instrument is within a predetermined distance of the implantable device.

2. The surgical guidance system of claim 1, the detectable field having an intensity that varies with distance from the implantable device, and the control unit being configured to use the proximity sensor to determine the intensity of the detectable field.

3. The surgical guidance system of claim 2, the control unit being configured to determine that the distal end of the surgical instrument is within the predetermined distance of the implantable device in response to a determination that the intensity of the detectable field is equal to or greater than a threshold intensity.

4. The surgical guidance system of claim 1, comprising a notification unit in communication with the control unit and configured to notify a user of the surgical instrument that the distal end of the surgical instrument is within the predetermined distance of the implantable device.

5. The surgical guidance system of claim 4, the notification unit being configured to vibrate in response to a determination that the distal end of the surgical instrument is within the predetermined distance of the implantable device.

6. A surgical guidance system comprising:
an implantable device configured for attachment to an anatomical structure;
a surgical instrument having a proximal end and a distal end, the distal end of the surgical instrument defining a leading end of the surgical instrument during insertion into a patient and being movable relative to the implantable device while the implantable device is attached to the anatomical structure;
a surgical tool attached to the distal end of the surgical instrument, the surgical tool including one or more of: a laparoscopic grasper, scissors, calipers, forceps, a retractor, a scalpel, a lancet, rasps, a trocar, a harmonic scalpel, rongeurs, a dilator, a specula, a suction tube, a stapler, a needle, an ultrasonic cutter, a laser cutter, laparoscopic dissectors, a laparoscopic monopolar cautery, a laparoscopic bipolar cautery, and a colpotomizer;

a proximity sensor; and a control unit in communication with the proximity sensor and configured to use the proximity sensor to determine if the distal end of the surgical instrument is within a predetermined distance of the implantable device.

7. The surgical guidance system of claim 6, comprising a coiled wire connected to the implantable device.

8. The surgical guidance system of claim 7, the coiled wire being embedded within a portion of the implantable device.

9. The surgical guidance system of claim 8, the coiled wire being made of an electrically conductive material.

10. The surgical guidance system of claim 6, the distal end of the surgical instrument including a cutting element.

11. The surgical guidance system of claim 6, comprising a notification unit in communication with the control unit and configured to notify a user of the surgical instrument that the distal end of the surgical instrument is within the predetermined distance of the implantable device.

12. The surgical guidance system of claim 1, the proximity sensor being attached directly to the distal end of the surgical instrument and configured for insertion into the patient such that the proximity sensor is carried by the distal end of the surgical instrument into the patient during a surgical procedure.

13. The surgical guidance system of claim 6, the proximity sensor being configured for insertion into the patient.

14. A surgical guidance system comprising:

a surgical instrument having a proximal end and a distal end, the surgical instrument being movable relative to the implantable device, the distal end of the surgical instrument defining a leading end of the surgical instrument during insertion into a patient;

a surgical tool attached to the distal end of the surgical instrument, the surgical tool including one or more of: a laparoscopic grasper, scissors, calipers, forceps, a retractor, a scalpel, a lancet, rasps, a trocar, a harmonic scalpel, rongeurs, a dilator, a specula, a suction tube, a stapler, a needle, an ultrasonic cutter, a laser cutter, laparoscopic dissectors, a laparoscopic monopolar cautery, a laparoscopic bipolar cautery, and a colpotomizer;

an implantable device configured for attachment to an anatomical structure independent of the distal end of the surgical instrument;

a proximity sensor; and a control unit in communication with the proximity sensor and configured to use the proximity sensor to determine if the distal end of the surgical instrument is within a predetermined distance of the implantable device.

15. The surgical guidance system of claim 14, the implantable device including a tubular member having a hollow interior located between first and second ends of the implantable device.

16. The surgical guidance system of claim 1, wherein the implantable device is attachable to the anatomical structure independent of the distal end of the surgical instrument.

17. The surgical guidance system of claim 6, wherein the implantable device is attachable to the anatomical structure independent of the distal end of the surgical instrument.

18. The surgical guidance system of claim 1, the implantable device including a tubular member having a hollow interior located between first and second ends of the implantable device.

19. The surgical guidance system of claim 6, the implantable device including a tubular member having a hollow interior located between first and second ends of the implantable device.

20. A surgical guidance system comprising:

an implantable device configured for attachment to an anatomical structure and to emit a detectable field, the implantable device including a tubular member having a hollow interior located between first and second ends of the implantable device;

a surgical instrument having a proximal end and a distal end, the distal end of the surgical instrument defining a leading end of the surgical instrument during insertion into a patient and being movable relative to the implantable device while the implantable device is attached to the anatomical structure;

a proximity sensor attached to the distal end of the surgical instrument and configured to detect the detectable field; and a control unit in communication with the proximity sensor and configured to use the proximity sensor to determine if the distal end of the surgical instrument is within a predetermined distance of the implantable device.

21. A surgical guidance system comprising:

an implantable device configured for attachment to an anatomical structure, the implantable device including a tubular member having a hollow interior located between first and second ends of the implantable device;

a surgical instrument having a proximal end and a distal end, the distal end of the surgical instrument defining a leading end of the surgical instrument during insertion into a patient and being movable relative to the implantable device while the implantable device is attached to the anatomical structure;

a proximity sensor; and a control unit in communication with the proximity sensor and configured to use the proximity sensor to determine if the distal end of the surgical instrument is within a predetermined distance of the implantable device.

22. A surgical guidance system comprising:

a surgical instrument having a proximal end and a distal end, the surgical instrument being movable relative to the implantable device, the distal end of the surgical instrument defining a leading end of the surgical instrument during insertion into a patient;

an implantable device configured for attachment to an anatomical structure independent of the distal end of the surgical instrument, the implantable device including a tubular member having a hollow interior located between first and second ends of the implantable device;

a proximity sensor; and a control unit in communication with the proximity sensor and configured to use the proximity sensor to determine if the distal end of the surgical instrument is within a predetermined distance of the implantable device.

* * * * *